United States Patent [19]

Garbutt

[11] Patent Number: 5,266,685
[45] Date of Patent: Nov. 30, 1993

[54] NON-BITTER PROTEIN HYDROLYZATES

[75] Inventor: John T. Garbutt, Muscatine, Iowa

[73] Assignee: Grain Processing Corporation, Muscatine, Iowa

[21] Appl. No.: 878,812

[22] Filed: May 5, 1992

[51] Int. Cl.$^5$ .......................... C07K 3/18; A23J 1/12; A61K 35/78

[52] U.S. Cl. ................................. 530/370; 530/372; 530/373; 530/376; 530/378; 530/379; 530/360; 530/832; 530/407; 530/421; 426/656

[58] Field of Search ............... 530/407, 421, 379, 370, 530/372, 373, 376, 378, 360, 832

[56] References Cited

U.S. PATENT DOCUMENTS

| | | | |
|---|---|---|---|
| 3,950,529 | 4/1976 | Fischer et al. | 424/273 |
| 4,439,458 | 3/1984 | Puri | 426/330.5 |
| 4,514,427 | 4/1985 | Mitchell et al. | 426/271 |
| 4,557,927 | 12/1985 | Miyake et al. | 426/10 X |
| 4,675,196 | 6/1987 | Villa et al. | 426/271 |
| 5,021,248 | 6/1991 | Stark et al. | 426/26 |
| 5,152,897 | 10/1992 | Shibuta et al. | 210/639 |
| 5,182,130 | 1/1993 | Haralampu et al. | 426/310 |

OTHER PUBLICATIONS

Matthews, R. L. et al., "Removal of Limonin and Naringin from Citrus Juice by Styrene-Divinlybenzene Resins", *Food Technology*, Apr. 1990, pp. 130–132.

A. P. Ericson et al., "Recovery of Grapefruit Oil Constituents from Processing Waste Water Using Styrene-divinylbenzene Resins", *J. of Food Sci.*, 57 (1) 186–189, 1992.

Naipawer, R. E. et al., "The Isolation of Flavour Components from Foods by Distillation and Adsorption", *The Flavor Industry*, Aug. 1971, pp. 465–467.

Bryan, William L. et al., "Adsorption of Flavor Components from Aqueous Orange Peel Aroma Solutions", *Ind. Eng. Chem. Prod. Res. Dev.*, vol. 16, No. 2, 1977, pp. 257–261.

Clegg, K. M. et al., "Dietary enzyme hydrolysates of protein with reduced bitterness", *J. Fed. Technol.* (1974) 9, 21–29.

Clegg, K. M. et al., "Production of an enzyme hydrolysate of casein on a helogram scale", *J. Fed. Technol.* (1974), 9, 425–431.

Helbig, N. B., et al., "Debittering of Skim Milk Hydrolysates by Adsorption for Incorporation into Acidic Beverages", *J. of Food Sci.*, 1980, vol. 45, pp. 331–335.

Cogan, Uri, et al., "Debittering and Nutritional Upgrading of Enzyme Casein Hydrolysates", *J. Sci. Food Agric.*, 1981, 32 459–466.

Ma, C. Y. et al., "Production of Nonbitter, Desalted Milk Hydrolysates for Fortification of Soft Drinks and Fruit Juices", *J. of Food Sci.*, vol. 48 (1983), pp. 897–899.

Matsuoka, H., et al, "Purification and Debittering Effect of Aminopeptidase II from *Penicillium caseicolum*" *J. Agric. Food Chem.*, 1991, 39, 1392–1395.

Adachi, S., et al., "Separation of Peptide Groups with Definite Characteristics from Enzymatic Protein Hydrolysate", *Agric. Biol. Chem.*, 55 (4) 1991, 925–932.

Inouye, K., "Chromatographic Behaviors of Proteins and Amino Acids on a Gel Filtration Matrix, TSK-GEL Toyopearl", *Agric. Biol. Chem.*, 55 (8), 2129–2139, 1991.

(List continued on next page.)

*Primary Examiner*—Michael G. Wityshyn
*Assistant Examiner*—C. Sayala
*Attorney, Agent, or Firm*—Fitch, Even, Tabin & Flannery

[57] ABSTRACT

New protein hydrolyzates are produced by treating an aqueous solution of a protein hydrolyzate with an adsorptive resin functional to remove from the protein hydrolyzate bitter taste components, color and odor components and aromatic amino acids. The treated protein hydrolyzate solutions can be concentrated and dried if desired to powder form.

9 Claims, No Drawings

OTHER PUBLICATIONS

Tanimoto, Shinya-Ya, et al., "Enzymatic Modification of Zein to Produce a Non-Bitter Peptide Fraction with a Very High Fischer Ratio for Patients with Hepatic Encephalopathy", *Agric. Biol. Chem.*, 55 (4), 1119–1123, 1992.

Arai, Soichi, et al., "Enlarged-scale Production of a Low-phenylalanine Peptide Substance as a Foodstuff for Patients with Phenyketonuria", *Agric. Biol. Chem.*, 50 (11), 2929–2931, 1986.

Lopez-Bajonero, L. J. et al., "Enzymatic Production of a Low-Phenylalanine Product from Skim Milk Powder and Caseinate", *J. of Food Sci.*, 56 (4), 938–942, 1991.

Maeda, Akiko et al., "Peptic Hydrolysis of Bovine β-Lactoglobulin to Produce a Low-Phenylalanine Peptide Foodstuff for Phenylketonuria", *J. Agric. Biol. Chem.*, 51 (6), 1502–1507, 1987.

"Amberlite-Resin Selection Guide", SUPERCO (Division of Rohm & Haas), Bellefonte, Pennsylvania, 1990.

NON-BITTER PROTEIN HYDROLYZATES

This invention relates to protein hydrolyzates having particularly desired characteristics.

BACKGROUND OF THE INVENTION

Proteins can be readily hydrolyzed by acid or enzymes to yield water-soluble hydrolyzates consisting of amino acids and peptides. However, the protein hydrolyzates usually exhibit a very bitter flavor and solutions thereof are highly colored with characteristic odors. Removal of the undesirable flavor, color and odor from protein hydrolyzates presents problems. Materials such as activated carbon, bentonite, zeolites and ion exchange resins have been employed in attempts to remove these undesired characteristics but such attempts have either been relatively ineffective or result in high product losses or are expensive.

Currently the medical conditions of hepatic encephalopathy and phenylketonuria are treated with diets formulated with pure amino acids with reduced levels of aromatic amino acids. Such formulations are not only very expensive but are not well accepted by the patient due to their undesirable flavors and odors. Many of these patients must remain on these diets for very long periods of time, thus making it a very expensive program indeed. Protein hydrolyzates from inexpensive protein sources having improved characteristics with respect to flavor, color and odor and having low levels of aromatic amino acids fulfills a real need in treating certain medical conditions as well as in other applications.

OBJECTS OF THE INVENTION

It is a principal object of this invention to provide protein hydrolyzates having bland flavor, little odor or color and having reduced levels of aromatic amino acids.

It is another object of this invention to provide a simple procedure to produce desirable protein hydrolyzates from widely available inexpensive protein sources.

SUMMARY OF THE INVENTION

In accordance with this invention there is produced a bland tasting protein hydrolyzate low in color and odor having high levels of branched chain amino acids (BCAA) and low levels of aromatic amino acids (AAA). The new protein hydrolyzates according to the invention are produced by treating an aqueous solution of a protein hydrolyzate with an adsorptive resin functional to remove from the protein hydrolyzate bitter taste components, color and odor components and aromatic amino acids such as tyrosine and phenylalanine. The treated protein hydrolyzate solutions can be concentrated and dried if desired to powder form.

The protein hydrolyzates which are treated in accordance with this invention can be a proteinaceous material of vegetable or animal origin which has been hydrolyzed by acid or enzyme methods well known in the art. Preferred from an economic standpoint are hydrolyzates of inexpensive, readily available protein materials such as corn gluten, soy protein, milk protein, and the like.

The adsorptive resins which are employed in accordance with this invention are polymeric resins, which function to remove bitterness, odor, color and aromatic amino acids from the protein hydrolyzates but not substantial amounts of branched chain amino acids. A preferred class of adsorptive resins for use are polymeric crosslinked resins composed of styrene and divinylbenzene such as, for example, the Amberlite series of resins, e.g., Amberlite XAD-2, Amberlite XAD-4 and Amberlite XAD-16, which are available commercially from Rohm & Haas Co., Philadelphia, Pa. Other polymeric crosslinked styrene and divinylbenzene adsorptive resins suitable for use according to the invention are XFS-4257, XFS-4022, XUS-40323 and XUS-40322 manufactured by Dow Chemical Company, Midland, Mich., and the like.

Treatment of protein hydrolyzates in accordance with the invention can be conducted in various manners such as by a batch treatment or more preferably by passing an aqueous solution of a protein hydrolyzate through a column containing the adsorptive resin. The column size depends upon the sample size and concentration of the aqueous protein hydrolyzate.

The protein hydrolyzate dissolved in water is preferably passed through a column of the adsorptive resin. The protein hydrolyzate solution should be free of insoluble material so as to not plug the column or impede flow therethrough. The concentration of the aqueous protein hydrolyzate solution can vary provided that it is not too viscous as to preclude reasonable flow rates. Generally the concentration of the aqueous protein hydrolyzate undergoing treatment can be in the range of about 1 to 20% by weight with concentrations of about 5-10% being preferred. The pH of the protein hydrolyzate solution can be in the range of pH 3 to 9 with pH values below 7 preferred. The flow rate of the protein hydrolyzate solution through the column should be slow enough to allow sufficient time for the undesired bitterness, color, odor and aromatic amino acid components to be adsorbed on the adsorptive resin. Column flow rates between one to five bed volumes/hour are generally satisfactory, with column flow rates between 2-3 bed volumes/hour preferred.

DESCRIPTION OF PREFERRED EMBODIMENTS

According to a typical preferred embodiment, a 5-10% aqueous solution of a protein hydrolyzate having a clear brown color and bitter flavor is flowed through a glass column filled with beads of Amberlite XAD-16 resin. The flow ratio is maintained at approximately 1-2 bed volumes/hour. The emerging effluent is monitored for solids content by such means as refractive index measurement. The emerging effluent is collected until the solids content thereof reaches a steady value indicating that absorption of components by the resin has ceased. The collected effluent substantially free of bitterness, color and odor components and aromatic amino acid can then be concentrated and dried such as by freeze drying or spray drying to yield a white, odorless solid product with a bland flavor and a low aromatic amino acid content. After the above purified effluent fraction has been collected the resin column can be washed with an appropriate alcohol such as methanol, ethanol or isopropanol of 80 to 100% alcohol concentration. The adsorbed components (color, odor, flavor and aromatic amino acid components) are removed from the resin by the alcohol and recovered in the resulting effluent. The excess alcohol remaining in the column is then washed out with 4-5 bed volumes of water and the purification column is ready to be used again.

The alcohol eluted fraction can be distilled to recover the alcohol and the remaining aqueous residue freeze dried to provide a product having a characteristic protein odor, a pale yellow color and a very bitter flavor. The product has a high (>75%) molecular weight protein content and is soluble in both alcohol and water. It is eminently suited for use as an animal feed.

EXAMPLE 1

Corn gluten hydrolyzate was prepared by treating a 10% slurry of corn gluten meal at pH 6.5 with one percent (dry basis) bacterial alpha amylase (CANALPHA, 600, available from Biocon (US) Inc., Lexington, Ky.) at 95° C. for 30 minutes. The slurry was adjusted to pH 4.6 with hydrochloric acid and 0.5% (dry basis) glucoamylase (ZYMATEC G-200, available from Enzyme Technology Inc., Ashland, Ohio) added and the slurry held at 60° C. for six hours. The slurry was then filtered and the filter cake was re-slurried in water to about 10% solids, adjusted to pH 8.2 with calcium hydroxide and 0.7% (dry basis) of a endoproteinase enzyme derived from *Bacillus licheniformis* (ALCALASE 2.5L, available from Novo Laboratories, Danbury, Conn.) added. The slurry was stirred at 60° C. for six hours, adjusted to pH 6.5 with 20% phosphoric acid and filtered with the aid of diatomaceous earth. The clear brown filtrate was spray dried to a tan powder and designated "corn gluten hydrolyzate".

Fifty grams of the above corn gluten hydrolyzate was extracted for two hours with 1250 milliliters of 95% ethanol and filtered. The clear brown filtrate was evaporated to dryness and redissolved in water to 8.0% w/v solids. The tan colored solution contained 82.1% protein (dry basis) and had a very bitter flavor.

One hundred fifty milliliters of the above solution was passed through a 2"×9" column of Amberlite XAD-2 resin at 5 milliliters per minute followed by a water wash. The aqueous effluents were collected and evaporated to a clear colorless solution containing 7.18% w/v solids and 76.3% (dry basis) protein. The flavor was quite bland whereas the initial feed to the column was colored and had a very bitter taste.

The adsorption column was then eluted with methanol and the resulting effluent evaporated to remove alcohol, and the solid residue taken up in 70 milliliters of water. This solution had a yellow color and contained 9.0% w/v solids. It had a very bitter flavor and a protein content of 83.6%, dry basis.

EXAMPLE 2

One hundred forty (140) milliliters of an aqueous solution of corn gluten hydrolyzate prepared as in Example 1 containing 9.1 grams of solids at pH 6.5 was flowed through a 1"×10" column of Amberlite XAD-16 at a rate of 4 milliliters per minute (1.8 bed volumes per hour) followed by water and increasing concentrations of methanol from 50 to 100%. The collected fractions were analyzed and the results shown below:

| Fraction | Solvent | ml | Color | Solids Recovery (g) | (%) |
|---|---|---|---|---|---|
| 1 | water | 112 | colorless | 0.09 | 0.98 |
| 2 | " | 370 | " | 3.62 | 39.8 |
| 3 | " | 102 | " | 0.38 | 4.1 |
| 4 | Methanol | 107 | yellow | 2.59 | 28.5 |
| 5 | " | 149 | yellow | 3.13 | 34.4 |
| Gluten Hydrolysate | | 140 | yellow | 9.10 | 100 |

Fraction 1 was water present in the column (void volume) which is displaced by the hydrolyzate liquid.

Fractions 2, 3, 4 and 5 were freeze dried and analyzed for protein, color, flavor and odor.

| Fraction | TCA Reaction[a] | Color | Protein[b] (% as is) | Flavor[c] | Odor |
|---|---|---|---|---|---|
| 2 | negative | white | 100 | bland | none |
| 3 | " | " | 99.8 | " | " |
| 4 | positive | pale yellow | 91.7 | bitter | " |
| 5 | positive | yellow | 82.5 | very bitter | characteristic |
| Gluten Hydrolysate | positive | tan | 89.9 | very bitter | characteristic |

[a]One part of a 4% w/w solution of sample plus one part of a 15% solution of trichloroacetic acid. The formation of a precipitate indicates the presence of large molecular weight protein.
[b]% Kjeldahl nitrogen × 6.25.
[c]Determined on 4% w/w solution.

Untreated corn gluten solution hydrolyzate and Fraction 2 were assayed for amino acid content with the results shown below:

| | Amino Acid, % | |
|---|---|---|
| Amino Acid | Solution Hydrolysate | Fraction 2 |
| Aspartic Acid | 5.82 | 3.71 |
| Threonine | 3.11 | 2.59 |
| Serine | 4.97 | 4.33 |
| Glutamic Acid | 23.41 | 25.68 |
| Proline | 6.86 | 4.30 |
| Glycine | 2.09 | 3.20 |
| Alanine | 9.56 | 13.10 |
| Valine | 4.07 | 2.95 |
| Methionine | 1.07 | not detected |
| Isoleucine | 3.82 | 1.72 |
| Leucine | 16.56 | 9.60 |
| Tyrosine | 5.14 | not detected |
| Phenylalanine | 4.70 | not detected |
| Histidine | 1.46 | 2.11 |
| Lipine | 1.03 | 2.51 |
| Arginine | 1.90 | 3.47 |
| Ammonia | 2.74 | 3.88 |

The results of these tests show that:

(1) Fractions 2 and 3 are obtained as colorless, odorless debittered products containing greater than 95% protein (Kjeldahl nitrogen×6.25) largely as low molecular weight peptides and amino acids. These fractions represent about 45% of the original gluten hydrolyzate solids.

(2) Fractions 4 and 5 represent the adsorbed solids and are recovered from the resin by elution with methanol. This material, containing 82 to 92% protein mostly as large molecular weight protein, has a very bitter flavor and is highly colored. It is soluble in both methanol and water.

(3) The absence of the aromatic amino acids, tyrosine and phenylalanine, in Fraction 2 is unexpected and renders the treated product particularly advantageous for applications wherein the content of aromatic amino acids must be kept at low levels, such as in diets which are recommended for the treatment of hepatic encephalopathy and phenylketonuria conditions.

EXAMPLE 3

Four hundred seventy milliliters of corn gluten hydrolyzate prepared as in Example 1 at pH 6.5 containing 21.8 grams of solids was flowed through a 1"×13" column of Amberlite XAD-16 (175 milliliter resin bed) at a rate of 5 milliliters per minute. The first 135 milliliters of effluent were discarded and the next 335 milliliters (Fraction 2) was collected at pH 6.4 and freeze dried to yield 5.5 grams, dry basis.

When all of the gluten hydrolyzate had been introduced into the column, the column was washed with water and an additional 580 milliliters (Fraction 3) was collected at pH 6.7 and freeze dried to yield 5.9 grams, dry basis.

The column was then washed with 84% methanol until 540 milliliters of clear yellow effluent (Fraction 4) were collected. This solution was evaporated to remove alcohol and the aqueous residue freeze dried to yield 10.4 grams, dry basis.

The above freeze dried fractions were analyzed as shown below:

| Fraction | grams | Recovery (%) | Protein (% DB) | Color | Flavor[a] | Odor |
|---|---|---|---|---|---|---|
| Gluten Hydrolysate | 21.8 | 100 | 93.4 | Tan | Bitter | characteristic |
| Fraction 2 | 5.5 | 25 | 95.4 | White | Bland | none |
| Fraction 3 | 5.9 | 27 | 94.5 | White | Bland | none |
| Fraction 4 | 10.4 | 48 | 88.9 | Yellow | Bitter | characteristic |

[a]Tasted as 4% w/w solutions at pH 6.5

As the results show, Fractions 2 and 3 represent a recovery of about 50% of the original solids as a colorless, odorless product with a bland flavor and containing approximately 95% protein. Because solutions of Fractions 2 and 3 do not form a precipitate with trichloroacetic acid (TCA) most of the protein exists as small peptides or amino acids. Whereas, Fraction 4 does form a precipitate with TCA indicating it has significant amounts of large molecular weight protein.

EXAMPLE 4

A soy hydrolyzate was prepared as follows: 100 grams of commercial soy protein isolate (PROFAM® 90, manufactured by Grain Processing Corportion, Muscatine, Iowa) was slurried in about 900 milliliters of water and adjusted to pH 5.5 with hydrochloric acid. About 0.5 gram of RHOZYME P-54 (a protease manufactured by Rohm and Haas Company, Philadelphia, Pa.) was added and the slurry maintained at 45-50° C. for 4-6 hours after which it was heated to about 90° C. for 10 minutes to inactivate the enzyme. The slurry was centrifuged and the hazy effluent was treated with 1-2% carbon (dry basis) at 60° C. for about 30 minutes and then filtered with the aid of diatomaceous earth. The clear brown filtrate was then further processed as described below.

Seventy-five milliliters of the soy hydrolyzate containing 7.16 grams of soluble solids was passed through a 1"×14" column of Amberlite XAD-16 resin (185 milliliters bed volume) at 3-5 milliliters per minute followed by a water wash. When the solids content of the effluent had dropped to zero, as determined by refractive index, the collected effluent (360 milliliters, colorless, slightly hazy, pH 5.6) was freeze dried to a white powder (Fraction 1).

The absorption column was washed with 88% methanol until the effluent showed zero solids. The brown colored effluent was evaporated to remove alcohol and the aqueous concentrate freeze dried to a tan/brown powder (Fraction 2).

| Fraction | Recovery g | Protein (%) | % DB | 3% w/w Solution Color | Odor | Flavor |
|---|---|---|---|---|---|---|
| Soy Hydrolysate | 7.16 | 100 | 92.6 | brown | characteristic | bitter |
| Fraction 1 | 5.0 | 70 | 90.3 | colorless | none | sli. bitter |
| Fraction 2 | 2.3 | 32 | 81.7 | brown | pungent | very bitter |

The amino acid contents of the above fractions were determined with the following results:

| | Amino Acid, % w/w | | |
|---|---|---|---|
| | Soy Hydrolysate | Fraction 1 | Fraction 2 |
| Aspartic acid | 10.55 | 11.50 | 8.98 |
| Threonine | 2.57 | 2.77 | 2.62 |
| Serine | 3.38 | 4.44 | 2.74 |
| Glutamic Acid | 16.10 | 19.10 | 12.20 |
| Proline | 3.79 | 1.79 | 7.91 |
| Glycine | 2.65 | 2.44 | 3.07 |
| Alanine | 3.14 | 3.61 | 2.01 |
| Valine | 3.35 | 3.02 | 4.22 |
| Methionine | 0.82 | 0.81 | 0.80 |
| Isoleucine | 5.05 | 4.06 | 6.94 |
| Leucine | 8.44 | 9.33 | 7.20 |
| Tyrosine | 2.72 | 2.36 | 3.23 |
| Phenylalanine | 3.67 | 0.03 | 10.98 |
| Histamine | 1.92 | 2.10 | 2.69 |
| Lysine | 5.33 | 7.12 | 2.30 |
| Arginine | 6.58 | 8.22 | 3.72 |

As in the case of corn gluten hydrolyzate, the initial aqueous Fraction 1 was colorless and odorless with a much improved flavor. Solids recovery from Fraction 1 was 70% and it contained 90% protein.

The most striking feature of the amino acid content of Fraction 1 was the almost quantitative removal of phenylalanine as well as a slight reduction in tyrosine content.

EXAMPLE 4

A sample of casein containing 82.2% protein, dry basis, was hydrolyzed as follows: One hundred grams of casein was slurried in water, adjusted to pH 8.2 with 10% calcium hydroxide and diluted to one liter. One milliliter of ALCALASE 2.5L (Novo Laboratories, Inc.) added and the slurry stirred at 60° C. for 4.5 hours. The pH was maintained at pH 8.2 by periodic addition of calcium hydroxide.

The slurry was adjusted to pH 6.4 with 10% phosphoric acid and filtered with the aid of Hyflo Supercel ™ (Johns-Manville Products Corporation) and the slightly hazy filtrate was freeze dried and designated, casein hydrolyzate. This material contained 91.4% protein, dry basis, formed a precipitate with trichloroacetic acid and had a bitter flavor.

Ten grams of casein hydrolyzate were dissolved in water and diluted to 120 milliliters. One hundred milliliters (7.5 grams) was passed through a 1"×13" column of Amberlite XAD-16 resin followed by a water wash.

Five hundred milliliters of aqueous effluent was collected (Fraction 1) and freeze dried to a white powder. The column was then eluted with 87% methanol and 335 milliliters of a slightly hazy, yellow effluent collected (Fraction 2). Methanol was removed by vacuum distillation and the aqueous residue freeze dried to a light tan powder. Analysis of casein hydrolyzate, Fraction 1 and Fraction 2, is shown below:

| Sample | grams | Solids Recovery | Protein (% DB) | 4% Solution | | |
|---|---|---|---|---|---|---|
| | | | | flavor | Color | TCA Reaction |
| Casein Hydrolysate | 7.5 | 100 | 91.4 | bitter | light yellow | + |
| Fraction 1 | 2.0 | 26 | 79.0 | bland | colorless | − |
| Fraction 2 | 5.7 | 75 | 91.3 | very bitter | light tan | + |

The amino acid contents of the above were determined and the results are shown below:

| | AMINO ACID CONTENT, WT % | | |
|---|---|---|---|
| Amino Acid | Casein Hydrolysate | Fraction 1 | Fraction 2 |
| Aspartic Acid | 56.30 | 83.4 | 4.86 |
| Threonine | 3.03 | 4.47 | 2.25 |
| Serine | 3.38 | 5.99 | 2.36 |
| Glutamic Acid | 17.58 | 26.22 | 12.79 |
| Proline | 9.79 | 0.93 | 12.13 |
| Glycine | 1.34 | 1.01 | 1.29 |
| Alanine | 2.50 | 2.55 | 2.05 |
| Valine | 5.58 | 3.29 | 5.77 |
| Methionine | 2.63 | 2.14 | 2.33 |
| Isoleucine | 5.25 | 2.31 | 5.68 |
| Leucine | 13.16 | 10.17 | 13.14 |
| Tyrosine | 5.43 | 2.25 | 6.20 |
| Phenylalanine | 5.04 | 0.33 | 6.30 |
| Histidine | 2.59 | 0.54 | 3.20 |
| Lysine | 6.88 | 6.17 | 6.44 |
| Arginine | 3.18 | 1.61 | 3.48 |

As the results show, Fraction 1 which has a very bland flavor has a significantly lower phenylalanine, proline, histidine and tyrosine content relative to the initial casein hydrolyzate. The lower contents of the aromatic amino acids along with its bland flavor make Fraction 1 an excellent candidate for use in diets for the treatment of hepatic encephalopathy and phenylketonuria conditions.

EXAMPLE 5

One hundred forty milliliters of corn gluten hydrolyzate (prepared as described in Example 1) containing 9.8 grams of solids was passed through a column (¾"×12") of Amberlite XAD-4 at 5 milliliters per minute at pH 6.4 followed by a water wash. The aqueous effluent was collected in two fractions (Fractions 1 and 2) and freeze dried. The column was then eluted with 100% methanol and the yellow/brown effluent collected and evaporated under vacuum to remove the alcohol. The residue was taken up in water and freeze dried. The pale yellow powder was designated Fraction 3.

Analyses of the above fractions are shown below:

| Fraction | grams | Recovery (%) | Protein (% DB) | Color | Flavor | Odor |
|---|---|---|---|---|---|---|
| Gluten Hydrolysates | 9.8 | 100 | 93.4 | Tan | bitter | characteristic |
| Fraction 1 | 0.9 | 9.2 | 94.4 | White | bland | none |
| Fraction 2 | 4.5 | 45.9 | 95.7 | White | " | none |
| Fraction 3 | 4.6 | 47.4 | 90.3 | Yellow | very bitter | characteristic |

The results show that the Amberlite XAD-4 resin yields a colorless, odorless product with a bland flavor and containing >95% protein. Solids recovery from Fractions 1 and 2 was 55%.

Both Fractions 1 and 2 did not form a precipitate with trichloroacetic acid indicating the absence of high molecular weight protein.

Those modifications and equivalents which fall within the spirit of the invention are to be considered a part thereof.

What is claimed is:

1. A process for producing an improved protein hydrolyzate from a protein hydrolyzate containing odor components, color components, bitterness components and aromatic amino acids which consists essentially of treating said protein hydrolyzate with a crosslinked adsorptive resin of styrene and divinylbenzene which functions to remove substantially from the protein hydrolyzate odor components, color components, bitterness components and aromatic amino acids.

2. A process in accordance with claim 1 wherein treating is conducted by passing a solution of the protein hydrolyzate through a bed of said adsorptive resin and recovering from said bed a protein hydrolyzate from which odor components, color components, bitterness components and aromatic amino acids have been removed.

3. A process in accordance with claim 2 wherein a liquid effluent from said bed is recovered and concentrated.

4. A process in accordance with claim 2 wherein a liquid effluent from said bed is recovered, concentrated and dried.

5. A process in accordance with claim 2 wherein after passing the solution of a protein hydrolyzate through said bed residual materials remaining on said bed are removed therefrom.

6. A process in accordance with claim 6 wherein a liquid solvent is employed to remove the residual materials from said bed.

7. A process in accordance with claim 5 wherein an alcohol is employed to remove the residual materials from said bed.

8. A process in accordance with claim 6 wherein the liquid solvent is removed from the residual materials.

9. A process in accordance with claim 5 wherein said residual materials removed from the bed are recovered and dried.

* * * * *

UNITED STATES PATENT AND TRADEMARK OFFICE
CERTIFICATE OF CORRECTION

PATENT NO. : 5,266,685
DATED : November 30, 1993
INVENTOR(S) : John T. Garbutt

It is certified that error appears in the above-identified patent and that said Letters Patent is hereby corrected as shown below:

Column 9, line 5, change "claim 6" to -- claim 5 --

Signed and Sealed this

Seventeenth Day of May, 1994

Attest:

BRUCE LEHMAN

Attesting Officer

Commissioner of Patents and Trademarks